(12) United States Patent
Joubert et al.

(10) Patent No.: US 8,159,216 B2
(45) Date of Patent: Apr. 17, 2012

(54) METHOD AND DEVICE FOR EDDY CURRENT IMAGING FOR THE DETECTION AND THE CHARACTERISATION OF DEFECTS HIDDEN IN COMPLEX STRUCTURES

(75) Inventors: Pierre-Yves Joubert, Sceaux (FR); Yohan Le Diraison, Cachan (FR); Jean Pinassaud, Paris (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 534 days.

(21) Appl. No.: 12/300,514

(22) PCT Filed: May 10, 2007

(86) PCT No.: PCT/FR2007/000791
§ 371 (c)(1),
(2), (4) Date: May 18, 2009

(87) PCT Pub. No.: WO2007/135265
PCT Pub. Date: Nov. 29, 2007

(65) Prior Publication Data
US 2010/0013468 A1 Jan. 21, 2010

(30) Foreign Application Priority Data
May 12, 2006 (FR) ...................................... 06 04255

(51) Int. Cl.
*G01N 27/72* (2006.01)
*G01R 33/032* (2006.01)

(52) U.S. Cl. ........................ 324/240; 324/244.1; 359/280
(58) Field of Classification Search .......... 324/228–243, 324/244.1; 359/280
See application file for complete search history.

(56) References Cited

U.S. PATENT DOCUMENTS

| 4,476,434 A * | 10/1984 | Collins et al. ................. 324/233 |
| 4,755,752 A | 7/1988 | Fitzpatrick |
| 5,053,704 A | 10/1991 | Fitzpatrick |
| 5,485,084 A * | 1/1996 | Duncan et al. ................ 324/225 |
| 5,610,517 A | 3/1997 | Ma et al. |
| 2003/0164700 A1 | 9/2003 | Goldfine et al. |
| 2006/0146328 A1 | 7/2006 | Decitre et al. |

FOREIGN PATENT DOCUMENTS
FR 2 856 791 12/2004
WO 02/25266 3/2002

OTHER PUBLICATIONS

Sotoshi Yamada et al., "Defect Images by Planar ECT Probe of Meander-Mesh Coils", IEEE Transactions on Magnetics, vol. 32, No. 5, Sep. 1996, pp. 4956-4958, IEEE Service Center, New York, NY.
Jean Pinassaud et al., "Quantitative Magneto-Optic Imager for Nondestructive Evaluation", Proceedings of the SPIE—The International Society for Optical Engineering SPIE—Int. Soc. Opt. Eng USA, vol. 5768, No. 1, 2005, pp. 196-203.

* cited by examiner

*Primary Examiner* — Jay Patidar
(74) *Attorney, Agent, or Firm* — Young & Thompson

(57) ABSTRACT

This eddy current imaging method includes the steps of:
positioning (72), in the vicinity of a large inspection region, elements for the measurement of a surface magnetic field,
generating (74, 92) a global exciting magnetic field over the observation inspection region,
measuring (76, 84) a resultant magnetic field at the surface, in the form of images,
processing (90) the images. The generating step (74, 82) involves generating a set of at least two exciting magnetic field waveforms; the measuring step (76, 86) involves measuring a set of configurations of the resultant magnetic field in the form of images; the step (90) of treating the images by combining them allows defects to be detected and the position and the nature thereof to be determined.

18 Claims, 7 Drawing Sheets

METHOD AND DEVICE FOR EDDY CURRENT IMAGING FOR THE DETECTION AND THE CHARACTERISATION OF DEFECTS HIDDEN IN COMPLEX STRUCTURES

The present invention relates to an eddy current imaging method and device for the detection and characterisation of defects concealed in complex structures, in particular in the fields of aeronautics and nuclear energy.

BACKGROUND OF THE INVENTION

The early detection and fine characterisation of defects, for example of cracks, in for example aeronautical structures, are a major issue for the safety and maintenance of aircraft.

Detection by means of eddy currents using electromagnetic sensors is made difficult by the complexity of the structure, which generates parasitic signals preventing the images from being easily read, by the low penetration of eddy currents due to the skin effect, by the low spatial resolution of the sensors which are generally used, and by the low number of measurement configuration options allowed by conventional sensors.

Conventionally, the detection of cracks in riveted joints is performed locally with point eddy current sensors or by means of constructions with 4 or 5 elements which operate differentially on a limited observation region of approximately 10 mm in diameter. With these devices, defects are sought at the base of the rivets, in the region of a second plate for example of a riveted assembly of aeroplane plates, at a depth of approximately 1.6 mm.

The small dimensions of the sensors or the small number thereof do not allow the structure to be explored in depth and also do not allow the position in the plates and the dimensions of the defect to be characterised precisely, as the spatial resolution of the signals to be detected is far too high.

This is why eddy current imagers which provide a larger observation region of approximately 76 mm and a higher spatial resolution have been developed.

These magneto-optic imagers are disclosed in particular in documents U.S. Pat. No. 5,053,704 and FR 2 856 791.

Meanwhile, the current image-treatment procedures, which are used by recently developed optical imagers, are ineffective for the fine detection of defects which are buried beyond a depth of 1.5 mm because of the binary nature of the images and/or the large number of perturbation patterns in the signal, which make interpretation of the images unreliable.

The objective problem is the poor performance provided by the presently used imaging procedures in detecting and finely locating defects which are buried deep inside a complex structure.

SUMMARY OF THE INVENTION

It is an object of the invention to propose an imaging procedure which allows the position and dimensions of defects which are buried deep inside a complex structure to be determined, for example at a depth of more than 1.5 mm in a riveted assembly of aeroplane plates.

The invention accordingly relates to an eddy current imaging method for the detection and characterisation of defects concealed in a complex structure, comprising the steps of:
Positioning means for the measurement of a surface magnetic field, in the vicinity of a target material, a substantially planar inspection surface region,
generating a global exciting magnetic field in the target material over the whole region,
measuring a resultant magnetic field, produced by the target material, at the surface of the inspection region, in the form of an image, an image consisting of a plurality of values contained within an interval of at least three values, each value being associated with a quantity of the resultant magnetic field, sensed in the vicinity of a plurality of points in the inspection region,
characterised in that
the generating step involves generating a set of at least two exciting magnetic field waveforms in the target material, each distinct waveform being determined by a narrow frequency spectrum and an angle of orientation in the target material,
the measuring step involves measuring a set of configurations of the resultant magnetic field in the form of a set of images, each image being associated with a quantity and with a waveform of the exciting magnetic field, and
in that it comprises a step of processing the set of images by combining them, to detect a defect and determine the position and the nature thereof.

In accordance with particular embodiments, the method comprises one or more of the following features, individually or in any technically feasible combination:
each waveform can be orientated at an angle of view determined by the position and geometry of a defect;
the frequency spectrum of each waveform is selected as a function of the desired observation depth in the target material;
the set of waveforms of the exciting magnetic field is a time-division multiplex of the waveforms;
the set of waveforms of the exciting magnetic field is a frequency-division multiplex of the waveforms;
the waveforms have approximately the same energy;
each waveform is a sine wave of a different frequency;
the number of waveforms is less than 25;
a resultant complex magnetic field image is a plurality of values of a real or imaginary spatial component of the resultant magnetic field, sensed in the vicinity of a plurality of points in the inspection region;
the step of processing the raw images comprises:
a learning step, consisting of constructing a projection operator adapted to the detection of predetermined types of defect, on the basis of raw images acquired in an acquisition step on a standard which has a known structure comprising types of defect calibrated according to a selected measurement configuration,
a projection step, consisting of applying the projection operator, which was determined in the preceding step, to the raw images acquired in the acquisition step on a test sample in which defects are being sought, in accordance with the same predetermined configuration used in the preceding step, in order to obtain useful, useable images;
the step of constructing the projection operator comprises the steps of:
selecting from the standard a row of a transverse line across the structure and the hidden defects,
extracting the line of the selected row from each raw image to form a reference measurement matrix for the standard,
forming the variance-covariance matrix of the reference matrix,
determining a basis of eigenvectors of the variance-covariance matrix,
ordering the eigenvectors in accordance with an ordering of the associated eigenvalues, forming the projector matrix using the ordered basis of eigenvectors, the step of applying the projection operator comprises the steps of:

for each line row i, forming a row i measurement matrix as a set of the lines from row i of each raw image;

for each row i, forming the product of the projection operator and the row i measurement matrix;

for each eigenvector component of the projector, forming the corresponding image component by assembling the lines, associated with the row i products, of an equivalent component;

the method further comprises the step of:

filtering the images obtained at the end of the projection step;

the filtering of the useful images is a filtering of a type belonging to the family of integration processes, deconvolution processes and Wiener filtering;

the procedure further comprises the step of:

classifying and diagnosing the presence, location and type of defect in the structure;

the step of classifying and diagnosing defects is a procedure of the type belonging to the family of processes consisting of the processes of threshold decision, maximum likelihood and decision by neural network;

the eddy current imaging procedure further comprises a step of constructing a database on the basis of a set of standards;

The invention further relates to an eddy current imaging device for the detection and characterisation of defects concealed in a complex structure, comprising, positioning means in the vicinity of an inspection region, means for generating a global exciting magnetic field over the whole of the inspection region;

means for measuring a resultant magnetic field, produced by the target material, at the surface of the inspection region, in the form of an image, an image consisting of a plurality of values contained within an interval of at least three values, each value being associated with a quantity of the resultant perturbation magnetic field, sensed in the vicinity of a plurality of points in the inspection region, means for the control and coordination of the induction device and the imager, image treatment means, and the means for generating a magnetic excitation field are able to generate a set of at least two exciting magnetic field waveforms in the target material, each distinct waveform being determined by a narrow frequency spectrum and an angle of orientation in the target material, the measurement means are able to measure a set of configurations of the resultant magnetic field in the form of a set of images, each image being associated with a quantity and with a waveform of the exciting magnetic field, and the image processing means are able to process the set of images by combining them, to detect a defect and determine the position and the nature thereof.

In accordance with particular embodiments, the device comprises one or more of the following features, individually or in any technically feasible combination:

the measurement means comprise a sensor network of a type belonging to the set consisting of coils, micro-coils, Hall probes, GMR (giant magnetoresistance) and GMI (giant magnetoimpedance); and the measurement means comprise a linear magneto-optic imager consisting of an optical device, a linear magneto-optic garnet and photodetection means.

BRIEF DESCRIPTION OF THE DRAWINGS

The invention may be better understood upon reading the following description of an embodiment, provided purely by way of example and made in reference to the drawings, in which:

FIG. 9 is a flow chart of a variant of the processing method of FIG. 5, in which a database of a plurality of calibrated standard samples is built up and made use of.

DETAILED DESCRIPTION OF THE PREFERRED EMBODIMENTS

Figure 1:
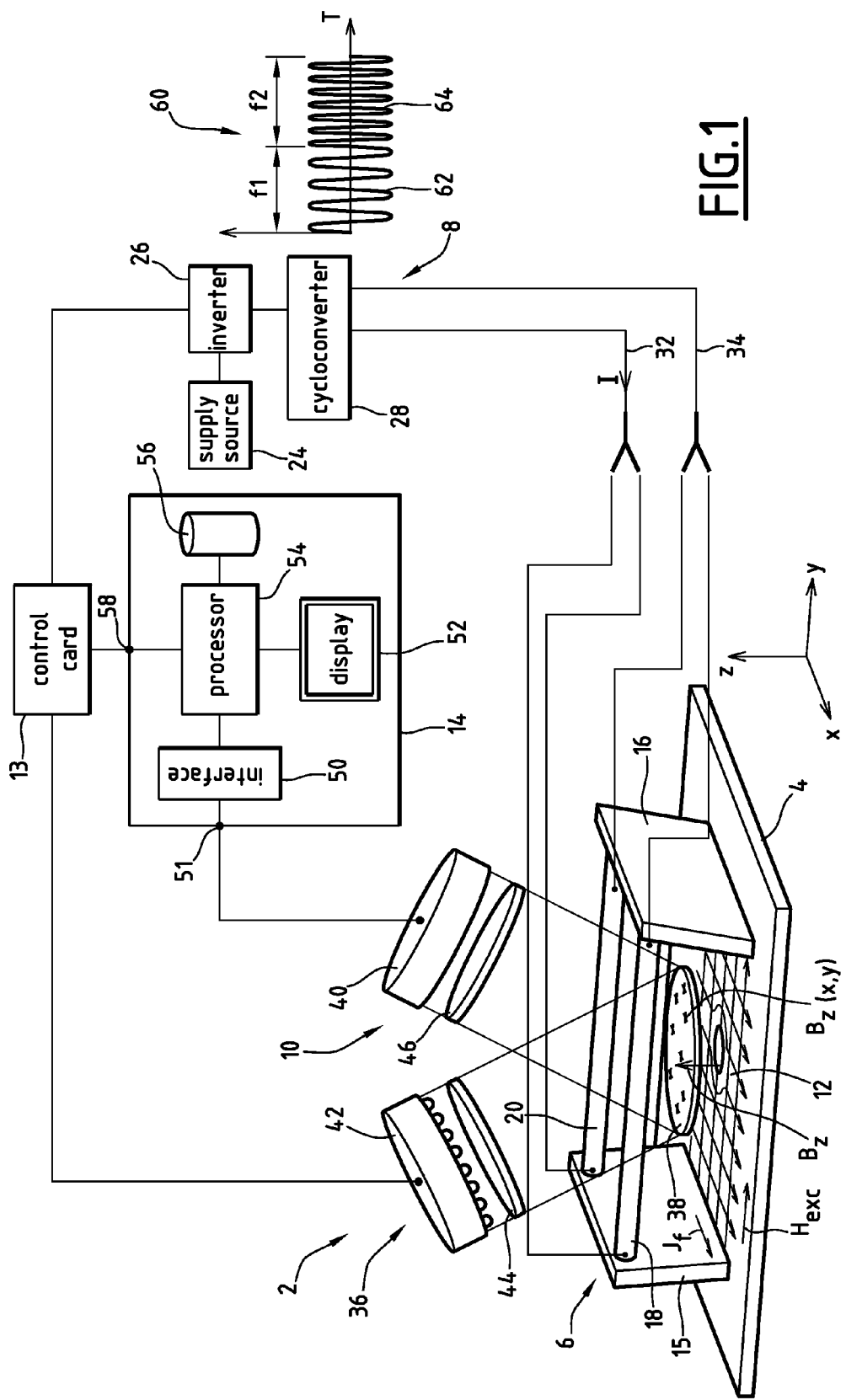
FIG. 1 is a general view of an embodiment of the eddy current imaging device according to the invention.

FIG. 1 schematically represents an embodiment of an eddy current imaging device 2 according to the invention. The imaging device 2 is disposed on the surface of a target material 4 and comprises an eddy current inductor 6, supplied by an alternating current generator 8, a field measurement device 10, in this case a magneto-optic imager, operating over a large inspection region 12 and synchronised with the inductor 6 by a dedicated digital synchronisation and control card 13.

The eddy current imaging device 2 further comprises a calculator 14 for controlling the various imaging and image processing tasks.

The inductor 6 comprises a magnetic circuit consisting of a first and a second magnetic pole 15, 16 allowing a uniform field $H_{exc}$, oriented along an axis parallel to the surface of the target material 4, to be circulated, the y-axis being one component of a reference triplet (x,y,z) with the z-axis defining the normal to the surface of the inspection region 112 of the target material.

The inductor 6 causes the uniform field $H_{exc}$ to circulate from one pole to the other by virtue of the presence of a first and second excitation coil 18, 20, passed through by alternating currents I supplied by the generator 8.

The excitation coils 18, 20 are supplied with alternating currents I with sinusoidal waveforms and with a frequency which can be adjusted over a wide range (for example 10 Hz, 10 MHz), provided by the current generator 8, which consists of a supply source 24 of continuous current, an inverter 26 which converts direct current into alternating current, and a cycloconverter 28.

The current generator 8 is connected to the coils 18, 20 via two branches of a first supply cable 32 connected on the side of the magnetic pole 15 and via two branches of a second supply cable 34 connected on the side of the second magnetic pole 16.

The alternating current generator 8, which has an adjustable frequency, is provided with an input 35 for providing the frequency setting of the current signal waveform.

In a variant, a second inductor, which is not shown in this document and which is oriented perpendicular to the first inductor, may be added.

The device 10 for measuring the magnetic field is in this case of the linear magneto-optic type. It comprises an optical device 36, a magneto-optic material 38 and photodetection means 40.

The optical device 36 comprises a light source 42, a polariser 44 and an analyser 46. The polariser 44 and the analyser 46 are conventional and known to the person skilled in the art. The light source 42 in this case consists of a matrix of electroluminescent diodes.

The optically active material, in this case a linear magneto-optic garnet, is positioned between the polariser 44 and the analyser 46 in the optical path and disposed in the vicinity of the surface of the inspection region of the target material 4. The assembly of the polariser 44, magneto-optic garnet 38 and analyser 46 forms a magneto-optic light modulator.

The photodetection means 40 are in this case an analogue CCD camera associated with a video capture card.

In a variant, the measurement device 10 is a sensor network of the type belonging to the set consisting of coils, microcoils, Hall probes, GMR (giant magnetoresistance) and GMI (giant magnetoimpedance), and other types of magnetic sensors.

The calculator 14 comprises an interface 50, for example of the USB type, for receiving video data supplied by the capture card at a video input 51.

The calculator 14 further comprises a visual display 52, in this case a liquid crystal display, and a processor 54 for image treatment and imaging task coordination, the processor 54 being connected to a database 56 in the form of memories of a conventional type.

The calculator 14 further comprises an output 58 for controlling the dedicated digital synchronisation and control card 13.

In this case, two sinusoidal current waveforms 62, 64 are produced by the current generator 8, each waveform 62, 64 having an associated frequency f1, f2 and forming a time-division multiplex 60 of two sine waves of different frequencies and substantially equal energies. In this case, f1 is 100 Hz whilst f2 is 700 Hz.

In a variant, the waveforms are sine waves which each have a narrow band spectrum.

In a variant, the number of waveforms is between 3 and 25.

In a variant, the two current waveforms are emitted simultaneously and form a frequency-division multiplex of two sine waves of distinct frequencies.

Figure 2:
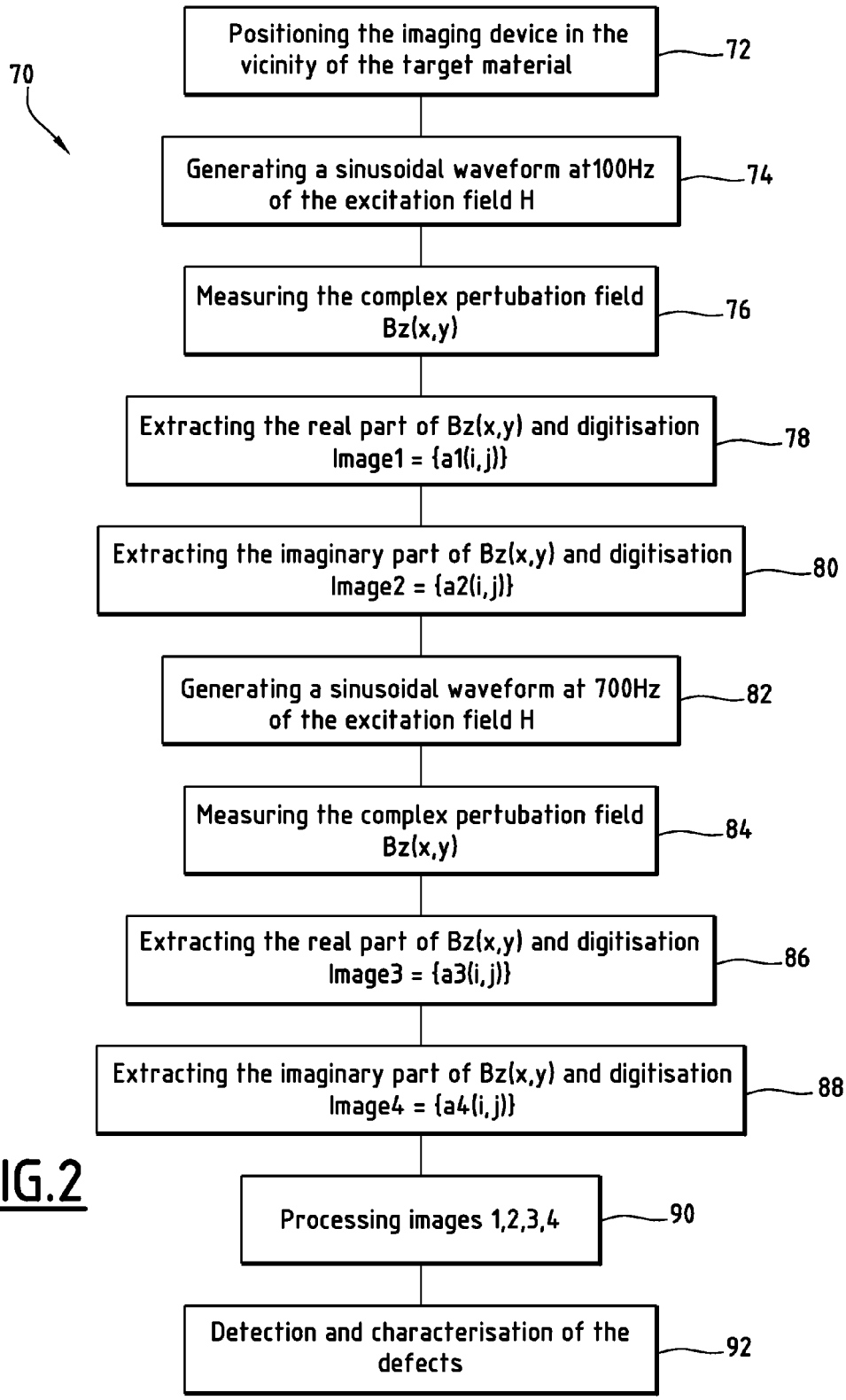
FIG. 2 is a flow chart of an embodiment of the imaging procedure according to the invention.

FIG. 2 shows an embodiment of the imaging process used in accordance with the invention. The imaging procedure 70 comprises a set of successively executed steps.

In a first step 72, the imaging device 2 is positioned in the vicinity of the region 12 of the target material 4 containing a sample to be tested. In the following step 74, the alternating current generator 8 generates the first waveform 62 of sinusoidal current at a frequency f1 of 100 Hz, and this allows the excitation field $H_{exc}$ to be produced in the region of the inductor 6 oriented along the y-axis of FIG. 1.

Thus, a current sheet referred to as $J_F$ in FIG. 1, is induced locally uniformly and oriented along the x-axis of FIG. 1 in a large inspection region 12, in this case greater than 75 mm in diameter. Upon encountering a buried structure with an electromagnetic impedance distinct from that of the homogeneous plate material, the currents $J_F$ vary in the trajectory and distribution thereof, thus creating a magnetic perturbation field which modulates the resultant magnetic field, in this case oriented along the z-axis as shown in FIG. 1, in which a circular rivet structure is shown.

It should be noted that in the case of a linear structure oriented along the y-axis, it is advantageous to orient the inductor parallel to the y-axis as in FIG. 1.

In a variant, in the case where a second inductor is available, it is possible to generate a second excitation field which in combination with the first allows an excitation field injection angle to be obtained.

Thus, each waveform can be oriented and may be adapted to an optimal viewing angle of the structure being tested.

Subsequently, in a step 76, the measurement of the complex resultant magnetic field at the surface of the inspection region 12 is performed.

In this case, the z-axis component of the complex magnetic field $B_z(x,y)$ is measured. This measurement must be taken with a sufficient sampling interval, the meaning of Shannon, in both the x and the y direction and may be obtained for the modulus or phase, or even for the real or imaginary part.

In a variant, another complex field component is measured, for example $B_x(x,y)$ or $B_y(x,y)$.

In the following step 78, the real part of the sampled magnetic field is extracted and thus forms a first raw image labelled Image 1, where Image $1=[a_1(i, j)]$.

Subsequently, the imaginary part of the same sampled field $B_2(x,y)$ is extracted in the step 80 to form a second raw image labelled Image 2, where Image $2=[a_2(i, j)]$.

In the following step 82, the alternating current generator 8 generates a second sinusoidal current waveform at a frequency f2 of 700 Hz, allowing the excitation field $H_{exc}$ to be generated. In step 84, the resultant complex field $B_z(x,y)$ is therefore measured.

In the subsequent step 86, the digitised real part of this field $B_z(x,y)$ is extracted so as to form a third raw image labelled Image 3, where Image $3=[a_3(i, j)]$.

In the following step 88, the imaginary part of the sampled field $B_z(x,y)$ is extracted so as to form a fourth raw image labelled Image 4, where Image $4=[a_4(i, j)]$.

The set of raw images obtained for the different frequencies is representative of phenomena which occur at the different depths f1 and f2 (skin effect) and thus constitutes different views of the same situation.

Thus, a frequency spectrum of each waveform is selected as a function of a desired observation depth in the target material 4.

The set of digitised data, forming the four raw images Image 1, Image 2, Image 3, and Image 4, is stored in the calculator 14 then processed in a raw image processing step 90.

After the raw image processing 90, useful, useable image components are obtained, allowing the detection and characterisation of hidden defects and thus the final diagnosis performed in step 92.

It is to be noted that if the sampling along the x and y-axes has to satisfy the Shannon condition, the complex field components are digitised in accordance with an amplitude of at least 2 bits, i.e. a vector of dimension greater than or equal to 2. In this case, it will be assumed that the amplitude of a measured complex magnetic field component $B_z(x,y)$ is coded in 12 bits.

It is also to be noted that in this case, the measurement of the complex field is carried out within the scope of a synchronous detection successively applied to the different excitation frequencies of the inductor 6, and coordinated by means of the dedicated digital synchronisation and control card 13.

In a variant, in the case of a simultaneous multiple synchronous detection, each measurement is applied to one of the frequency components making up the alternating excitation signal feeding the inductor 6 (and this corresponds to frequency-division multiplexing.)

The processing 90 of the raw images will now be disclosed in detail on the basis of raw images of a test sample and based on the characterisation of a standard of which the structure and defects are known a priori.

Figure 3:
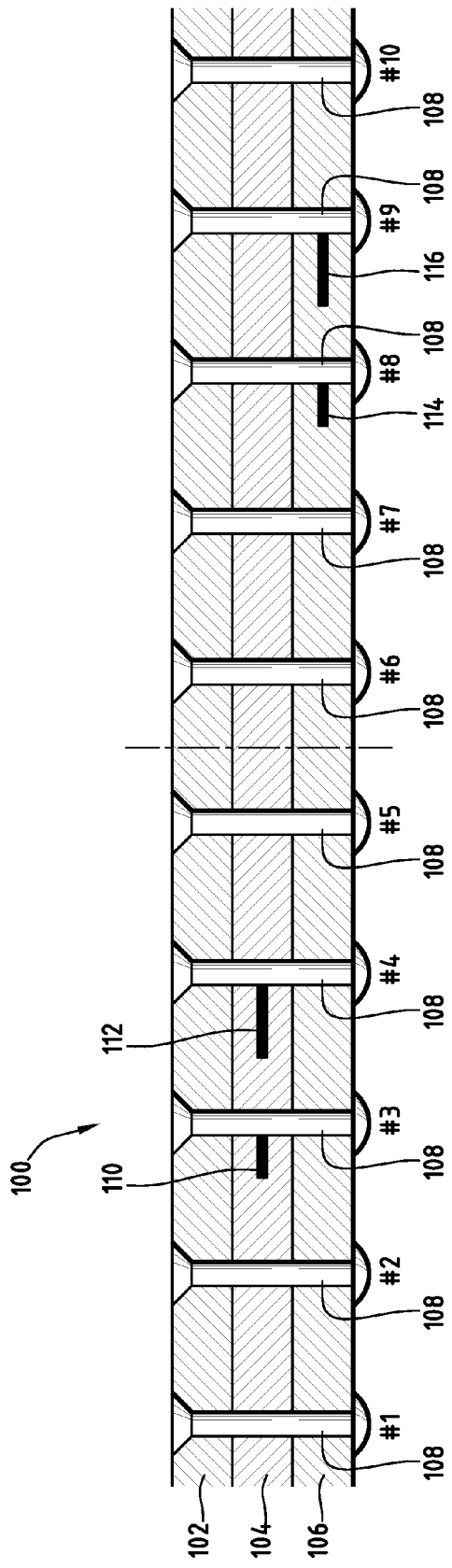
FIG. 3 is a transverse section of a test sample comprising a riveted structure with defects.

FIG. 3 shows an example test sample 100 comprising a riveted structure made up of three plates or sheets 102, 104, 106 of aluminium alloy (conductivity of 20 MS/m, relative permeability equal to 1) with a thickness of 3 mm, each comprising rivets 108 with a diameter of 4 mm, spaced regularly at 25 mm, both sound and with deep cracks. Ten rivets are shown in this case and the rivets 108 are numbered #1 to #10 from left to right in FIG. 3.

A first and second crack 110, 112, of what is known as type 1, extending respectively over a length of 7 and 12 mm for 100 μm of opening, are each located on the second plate 104 and buried at 3 mm in the region of the rivets numbered #3 and #4 respectively.

A first and second crack 114, 116, of what is known as type 2, extending respectively over a length of 7 and 12 mm for 100 μm of opening, are each located on the third plate 104 and buried at 6 mm in the region of the rivets numbered #8 and #9 respectively.

Figure 4:
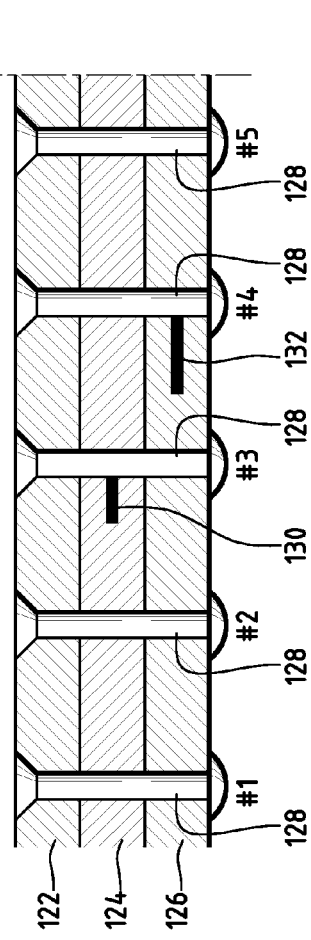
FIG. 4 is a transverse section of a standard riveted structure with a plurality of calibrated defects.

FIG. 4 shows a section through the structure of a standard 120, comprising a set of five rivets 128 which are spaced in each case at 25 mm, are numbered #1 to #5 from left to right in the figure and are affected by two types of defect.

The structure 120 is composed of a stack of three metal plates with a thickness of 3 mm, with a first plaque 122 and a second and third plaque 124 and 126. As for the test sample 100, the three plaques are made of aluminium and exhibit a conductivity of 20 MS/m and a relative permeability equal to 1.

A first crack 130 of type 1 with a length of 12 mm is buried in the second plate 124 at the base of rivet #3 and a second crack 132 of type 2 with a length of 12 mm is buried at the base of rivet #4 in the third plate 126.

Figure 5:
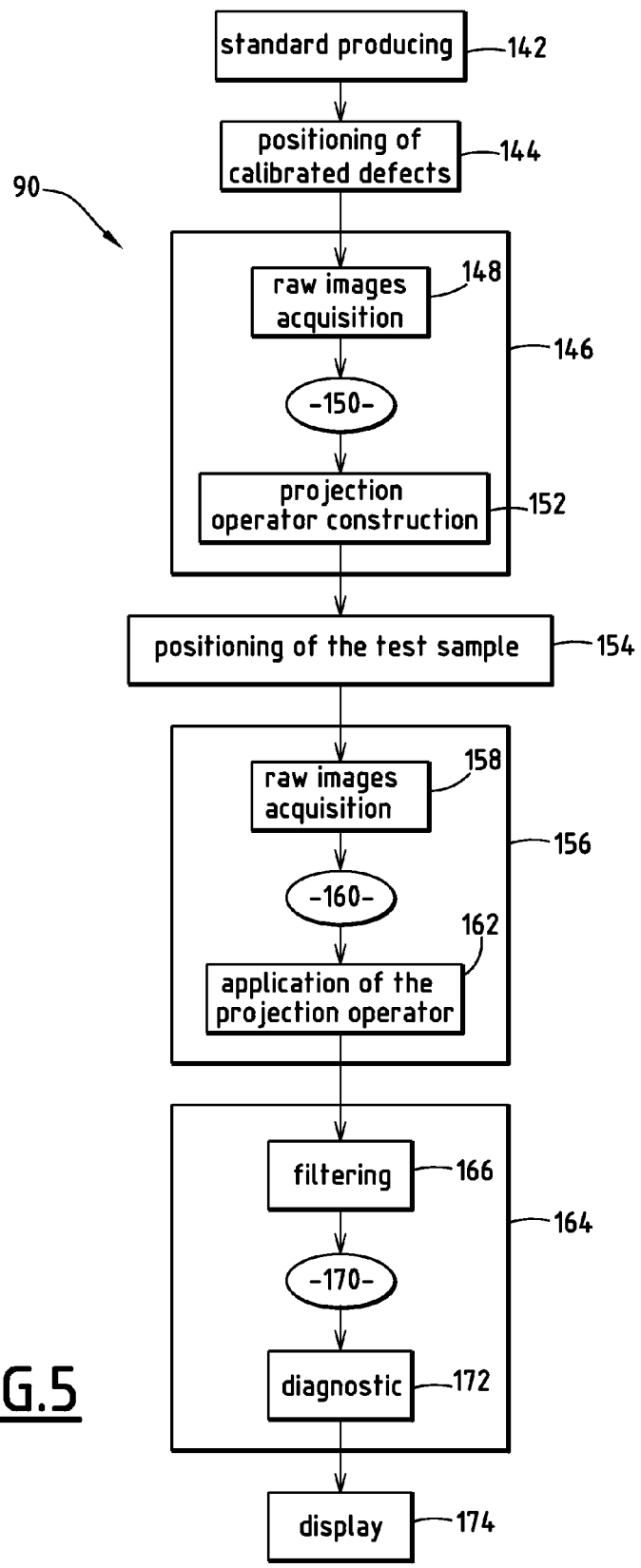
FIG. 5 is a flow chart of an embodiment of the imaging method according to the invention.

FIG. 5 shows the image processing method 90 in full.

Initially, in a first step 142, the standard 120 as shown in FIG. 4 is produced and has characteristics identical to the structure to be checked, i.e. a stack of three alloy plates riveted by rivets spaced regularly at 25 mm.

In the following step 144, calibrated defects are positioned, of the same type as those to be detected in the structure of FIG. 3 and shown in FIG. 4.

Subsequently, a learning step 146 follows, in which in accordance with the construction step 152, a projection operator is constructed, capable of highlighting the defects of type 1 and 2 which are being sought, on the basis of the raw images 150 acquired in the acquisition step 148 on the standard 120 with riveted joints comprising calibrated defects which are known a priori.

Figure 6:
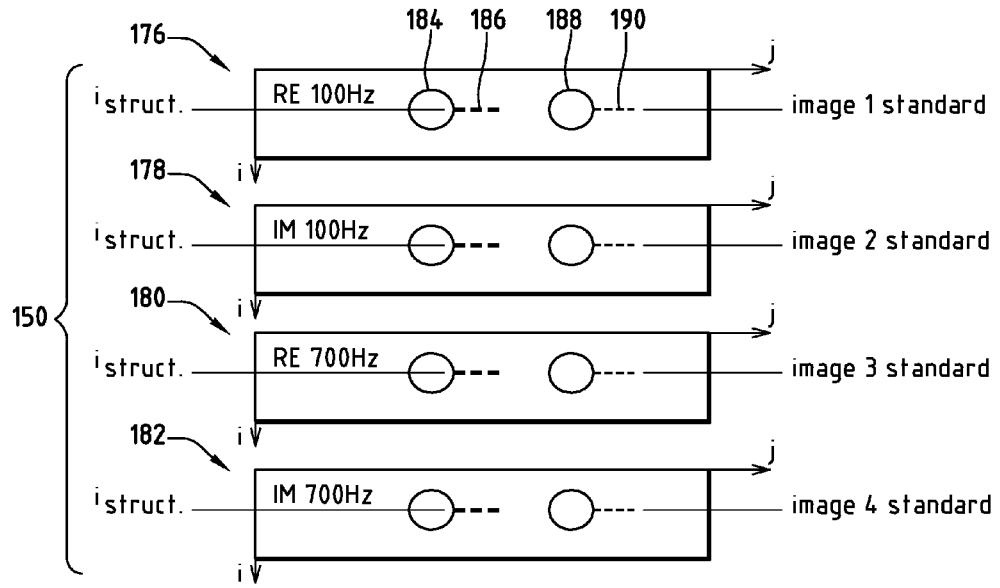
FIG. 6 is a view of the set of raw images obtained during the measurement carried out on the calibrated standard with the imaging device of FIG. 1.

The set of raw sample images 150 of the standard is shown schematically in FIG. 6.

The number and selection of analysis frequencies will influence the relevance of the determined projection operator.

Subsequently, in step 154, the sample 100 with riveted joints to be tested is positioned.

In the following step 156, the projection operator determined in step 152 is applied, in accordance with the application step 162, to the raw images 160 acquired in accordance with the application step 158, under the same experimental conditions as in step 148. In this step 156, which is a deconvolution step, a new series of raw images is provided at the end of 162, some of which contain information on the defects to be detected.

In the following step 164, filtering 166 is carried out, allowing the defect information, provided at the output of step 162 in the form of a set of components 170, to be displayed better, along with a diagnostic step 172 for making a decision as to the classification of the detected defects.

Figure 7:
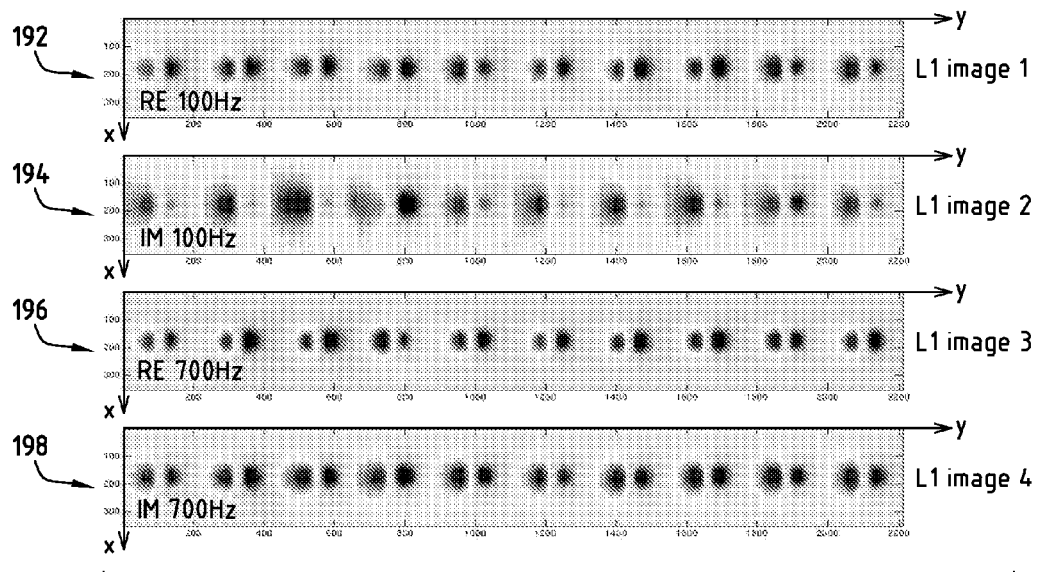
FIG. 7 is a view of the set of raw images obtained from the test sample during measurements carried out with the imaging device of FIG. 1.
Figure 8:
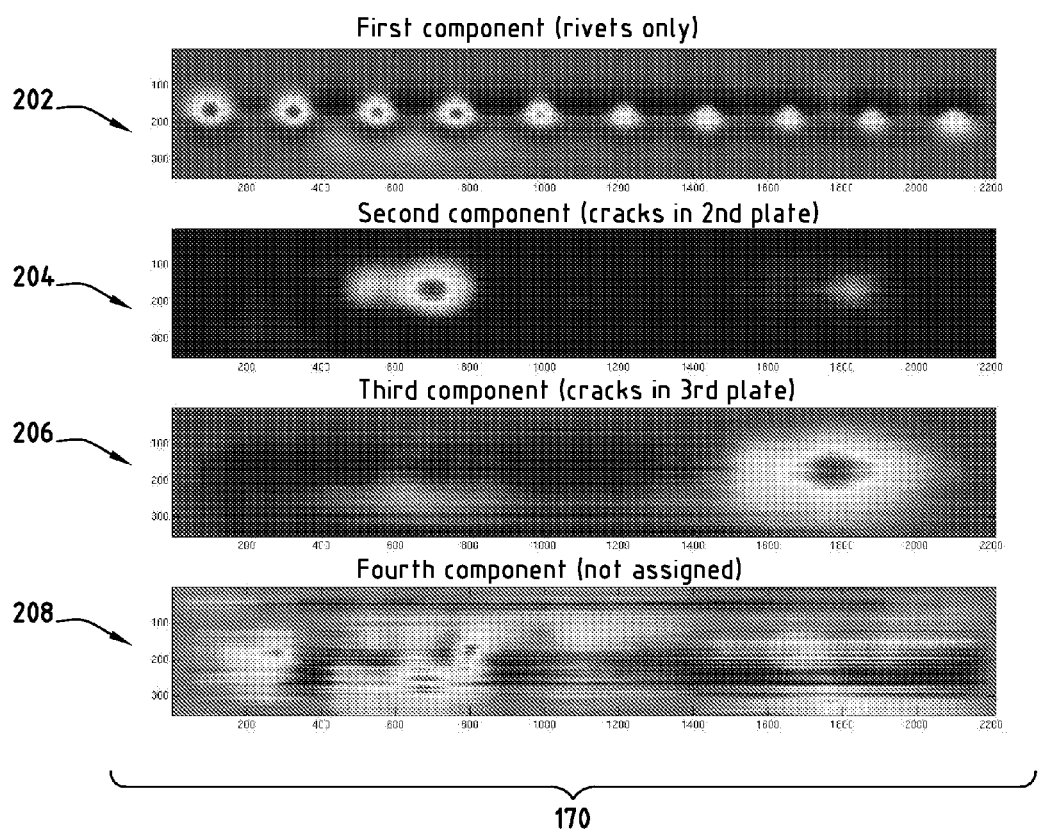
FIG. 8 is a view of the set of image components obtained after the processing step of FIG. 5.

The set of raw images 160 and the set of components 170 are shown respectively in FIGS. 7 and 8 and correspond to real measurements.

In the final step 174, the results of the diagnosis are displayed.

Over the course of the learning step 146, in the first acquisition step 148, the measurement paths are selected in a sufficient number to locate the three relevant sources of perturbations in the resultant field: rivets (structure), cracks in plate 2 (type 1 defects), cracks in plate 3 (type 2 defects). In this case, at least two frequencies are required which allow four measurement paths to be constituted, real and imaginary parts each being comprised as one measurement path.

In the example of the standard 120 provided in this case and shown in FIG. 3, f1=100 Hz has been set for one observation depth of 11 mm and f2=700 Hz has been set for a penetration depth of 4.3 mm for the electromagnetic radiation.

Thus, the second frequency f2 allows the type 1 defect to be seen together with the rivet whereas the first frequency f1 allows the type 2 defect to be seen with the rivet. Four raw images 150 of the standard 120 are thus obtained and will be used to define the convolution operator.

In step 152, the convolution operator, in this case a projection operator, is constructed from the set 150 of four raw standard images shown schematically in FIG. 6.

The first raw image 176 is an image of the real part of the complex resultant field at the frequency of 100 Hz, whereas the second raw image 178 is an image of the imaginary part of the complex resultant field at the frequency of 100 Hz.

The third raw image 180 is the real part of the field measured during induction at an excitation frequency of 700 Hz, whereas the fourth raw image 182 is the imaginary part of the field for an excitation frequency of 700 Hz.

The first raw image 176 shows the positions of two rivets 184, 188 in the vicinity of which the defects are located, namely rivet #3 and rivet #4, the former 184 being affected by a crack 186 of type 1 and the fourth rivet 188 being affected by a crack 190 of type 2. These defect structures are not generally clearly visible in the raw images. They are provided in this case for location based on a priori knowledge in order to allow the construction of the projection operator.

During the construction 152 of the projection or convolution operator, four lines of the same position are taken in the four measurement paths 176, 178, 180, 182, for example the row i line, denoted $i_{struc}$, which passes through the rivets and defects. These four lines form the reference measurement matrix $M_{ref}(i)$, The variance-covariance matrix $M_{ref}(i) \cdot M^T_{ref}(i)$ is calculated, where $M^T_{ref}(i)$ represents the transpose of the reference measurement matrix of line row i, $M_{ref}(i)$.

The four eigenvectors of this variance-covariance matrix are subsequently determined in a projection matrix $V_{proj}$ of dimension 4×4.

By projecting $M_{ref}(i)$ onto each projection vector in accordance with the operation $V_{proj} \cdot M_{ref}(i)$, a new matrix is obtained, the four lines or components of which correspond respectively to the most significant physical sources of perturbation contained in the four lines of $M_{ref}(i)$. In this case, only three sources are relevant, rivets, crack in plate 2, crack in plate 3. By knowing a priori the position of the reference cracks in the standard 120 which was used to construct $V_{proj}$, it is made possible to identify which components the eigenvectors correspond to.

Conversely, it is also possible to identify which eigenvector allows which source to be viewed. The eigenvectors can thus be ordered in $V_{proj}$ by a permutation such that it is known in advance in which component 1 to 4 the three relevant sources will appear.

In general, the eigenvectors correspond to the energies emitted by the different types of defect. If it is chosen to order the components in the order: component 1—rivet; component 2—plate 2 crack; component 3—plate 3 crack; component 4—none; then learning is complete.

In the course of the projection step 156, the acquisition step 158 involves taking measurements on the test sample 100 under the same experimental conditions as for step 148 for the standard 120. The four measurement paths or the set 160 of raw images as shown in FIG. 7 are thus obtained.

The set 160 of raw images comprises a first raw image 192 of the tested sample 100 while the exciting field $H_{exc}$ is at a frequency of 100 Hz and the real part of the magnetic field along the z-component is measured. The second raw image 194 represents the imaginary part of the same complex field for an exciting field at a frequency f1 of 100 Hz. The third raw image 196 represents the real part of the magnetic field measured for an excitation frequency f2 of 700 Hz. Finally, the fourth raw image 198 represents the imaginary part of the magnetic field measured for an excitation field with a frequency f2 of 700 Hz.

Based on these four raw images 192, 194, 196 and 198, the application of the projection operation 163 in accordance with the projection operator $V_{proj}$ is performed.

The four row 1 lines on the four raw images 192, 194, 196 and 198 which form the measurement matrix M(1) are applied to the projection operator or $M_{proj} \cdot M^T(1)$. A new matrix is obtained, the four lines of which are the components which will constitute the four row 1 lines of the four resulting images.

The application operation is repeated for all the row i lines for each image (from row 1 to row 350 in this example).

The four resulting images, in accordance with which the two types of default being sought in the rivet are classified, are thus obtained.

In step 166, the obtained data are filtered after the deconvolution operation 162, i.e. the projection of the measurement matrix. This filtering 166 takes place in order to bring this deconvolution into a form which can more readily be used for direct realisation or even for putting one of the diagnostic methods of step 172 into effect. The filtering 166 may be deconvolution, Wiener filtering or even an matched filtering.

In this case, an integration is carried out consisting of the sum of the samples accumulated from the left to the right of the image, line by line. Thus, the set 170 of four useful useable images or components is obtained.

The set 170 of useable useful images or components is represented in FIG. 8, which corresponds to real measurements. These useable useful images, obtained after filtering 166, represent a first component 202 on which only the rivets are visible, a second component 204 on which the cracks in the second plate or type 1 defects are visible, a third component 206 where cracks buried in the third plate or type 2 defects appear, and a fourth component 208 which does not a priori show any particular structure.

The diagnostic support step 172 uses a technique of the thresholding, maximum likelihood, or even neural network type.

Thus, an automatic decision as to the classification or location of the defects may more easily be made. The example disclosed below comprises only a single calibration standard as a comparison base.

Figure 9:
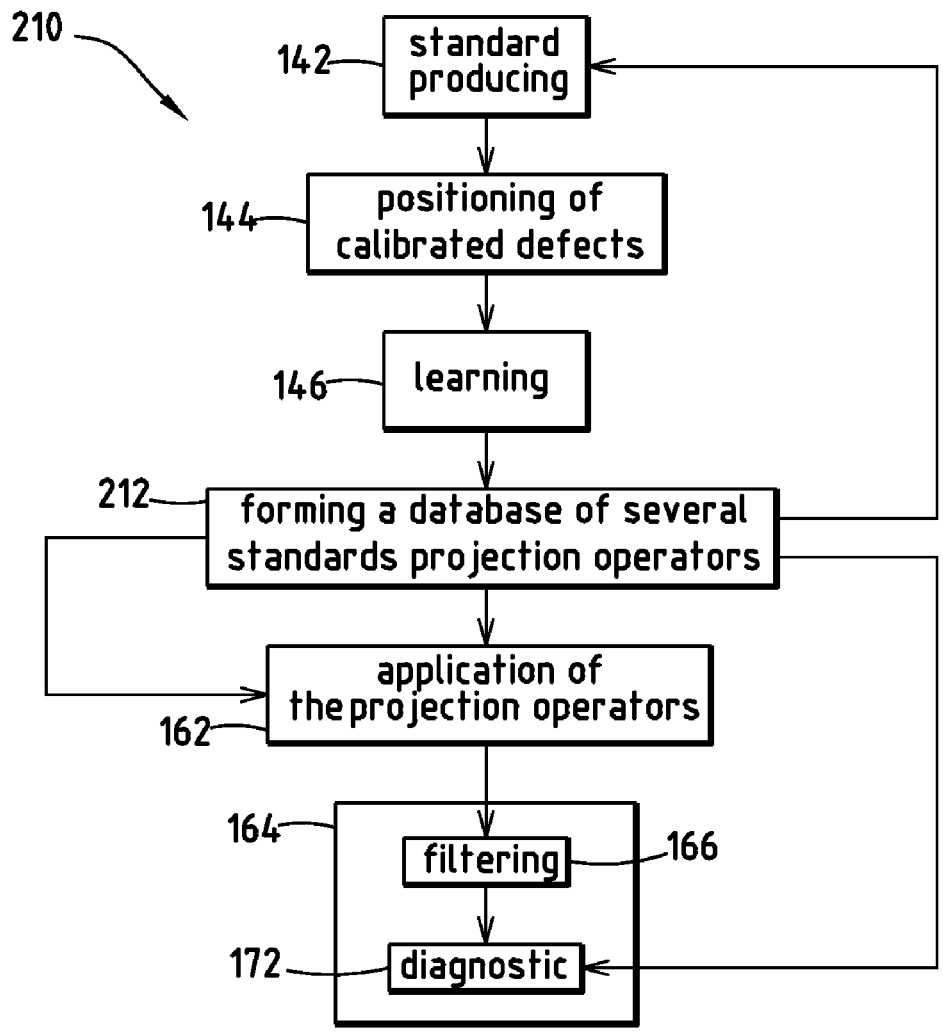

However, in a variant shown in FIG. 9, it is possible to extend the same type of measurement to standards with the same rivet structure but having defects of a different type and/or positioning, and thus to select configurations adapted to these additional or complementary configurations.

In fact, the steps 142, 14, 146, 162, 164, 166 and 172 described in FIG. 5 can be seen in FIG. 9.

A step 212, placed between 146 and 162, of forming a database of several standards with different calibrated defects forms a set of relevant projectors associated with the corresponding measurement conditions.

The data obtained from these additional test conditions and stored in step 212 make it possible to enrich the measurement system which is applied to the test sample in step 162 and the base of comparison signatures which can be used in carrying out the diagnostic support step 172.

Thus, it is possible to adapt the imaging system to particular structures and to make automatic searching effective for particular types of characteristic defect which are particularly being sought.

The invention claimed is:

1. An eddy current imaging method for the detection and characterization of defects concealed in a complex structure, comprising the steps of:

positioning (72) means (10) for measurement of a surface magnetic field in the vicinity of a substantially planar inspection surface region (12) of a target material (4);

generating (74, 82) a global uniform exciting magnetic field in the target material (4) over a whole of the inspection surface region (12); and measuring (76, 84) a resultant magnetic field produced by the target material (4) at the inspection surface region (12) in the form of a raw image, the raw image (192, 194, 196, 198) consisting of a plurality of binary data vectors having a dimension equal to or greater than 2, each vector being associated with a quantity of the resultant magnetic field, sensed in the vicinity of a plurality of points in the inspection surface region (12);

wherein the generating step (74, 82) comprises generating a set (60) of at least two exciting magnetic field waveforms (62, 64) uniformly in the target material (4), each distinct waveform (62, 64) determined by a narrow frequency spectrum and an angle of orientation in the target material (4), the frequency spectrum of each waveform being selected as a function of a desired observation depth in the target material (4), wherein the measuring step (76, 86) comprises measuring a set of configurations of the resultant magnetic field in the form of a set (160) of raw images (192, 194, 196, 198), each of the raw images (192, 194, 196, 198) associated with a quantity and with a waveform (62, 64) of the exciting magnetic field, and further comprising a step (90) of processing the set (160) of raw images by combining them, to detect a defect and determine the position and the nature thereof.

2. The eddy current imaging method according to claim 1, wherein each waveform (62, 64) is orientated at an angle of view determined by the position and geometry of a defect.

3. The eddy current imaging method according to claim 1, wherein the set (60) of waveforms (62, 64) of the exciting magnetic field is a time-division multiplex of the waveforms (62, 64).

4. The eddy current imaging method according to claim 1, wherein the set of waveforms (62, 64) of the exciting magnetic field is a frequency-division multiplex of the waveforms (62, 64).

5. The eddy current imaging method according to claim 1, wherein the waveforms have approximately the same energy.

6. The eddy current imaging method according to claim 1, wherein each waveform (62, 64) is a sine wave of a different frequency (f1, f2).

7. The eddy current imaging method according to claim 1, wherein the number of waveforms (62, 62) is less than 25.

8. The eddy current imaging method according to claim 1, wherein a resultant complex magnetic field image is a plurality of values of a real or imaginary spatial component of the resultant magnetic field, sensed in the vicinity of a plurality of points in the inspection region (12).

9. The eddy current imaging method according to claim 1, wherein the step of processing the raw images comprises:
   a learning step (146), consisting of constructing (152) a projection operator adapted to the detection of predetermined types of defect, on the basis of raw images (150) acquired in an acquisition step (148) on a standard (120) which has a known structure comprising types of defect calibrated according to a selected measurement configuration; and
   a projection step (156), consisting of applying (162) the projection operator, which was determined in the preceding step (146), to the raw images (160) acquired in the acquisition step (158) on a test sample (100) in which defects are being sought, in accordance with the same predetermined configuration used in the preceding step (148), in order to obtain useful, useable images (170).

10. The eddy current imaging procedure according to claim 9, wherein the step (152) of constructing the projection operator comprises the steps of:
   selecting from the standard (120) a row of a transverse line across the structure and the hidden defects;
   extracting the line of the selected row from each raw image to form a reference measurement matrix for the standard (120);
   forming the variance-covariance matrix of the reference matrix;
   determining a basis of eigenvectors of the variance-covariance matrix;
   ordering the eigenvectors in accordance with an ordering of the associated eigenvalues; and
   forming the projector matrix using the ordered basis of eigenvectors.

11. The eddy current imaging procedure according to claim 9, wherein the step of applying the projection operator comprises the steps of:
   for each line row i, forming a row i measurement matrix as a set of the lines from row i of each raw image (192, 194, 196, 198);
   for each row i, forming the product of the projection operator and the row i measurement matrix; and
   for each eigenvector component of the projector, forming the corresponding image component by assembling the lines, associated with the row i products, of an equivalent component.

12. The eddy current imaging method according to claim 9, wherein the procedure further comprises the step of:
   filtering (166) the useful images obtained at the end of the projection step (156).

13. The eddy current imaging method according to claim 12, wherein the filtering (166) of the useful images is a filtering of a type belonging to the family of integration processes, deconvolution processes and Wiener filtering.

14. The eddy current imaging method according to claim 9, wherein the method further comprises the step of:
   classifying and diagnosing the presence, location and type of defect in the structure.

15. The eddy current imaging method according to claim 14, wherein the step of classifying and diagnosing defects is a process of the type belonging to the family of procedures consisting of the processes of threshold decision, maximum likelihood and decision by neural network.

16. The eddy current imaging method according to claim 9, further comprising:
   a step (212) of constructing a database on the basis of a set of standards.

17. An eddy current imaging device (2) for the detection and characterization of defects concealed in a complex structure, comprising:
   means (6, 8) for generating a global uniform exciting magnetic field over a whole of a substantially planar inspection surface region (12) of a target material (4);
   means (10) for measuring a resultant magnetic field produced by the target material (4) at the surface of the inspection surface region (12) in the form of a raw image, the raw image consisting of a plurality of binary data vectors having a dimension equal to or greater than 2, each vector being associated with a quantity of the resultant perturbation magnetic field, sensed in the vicinity of a plurality of points in the inspection region;
   positioning means for positioning the means (10) for measuring the resultant magnetic field in the vicinity of the substantially planar inspection surface region (12) of the target material (4);
   means (13, 14) for control and coordination of the means (6, 8) for generating the exciting magnetic field and the means (10) for measuring the resultant magnetic field; and
   image processing means (14),
   wherein the means (6, 8) for generating a magnetic excitation field are configured to generate a set (60) of at least two exciting magnetic field waveforms (62, 64) in the target material (4), each distinct waveform (62, 64) being determined by a narrow frequency spectrum and an angle of orientation in the target material, the frequency spectrum of each waveform being selected as a function of a desired observation depth in the target material (4),
   wherein the measurement means (10) are configured to measure a set of configurations of the resultant magnetic field in the form of a set (160) of images (192, 194, 196, 196), each image being associated with a quantity and with a waveform of the exciting magnetic field, and
   wherein the image processing means (14) are configured to process the set of images by combining them, to detect a defect and determine the position and the nature thereof.

18. The eddy current imaging device (2) according to claim 17, wherein the measurement means (10) comprise a linear magneto-optic imager consisting of an optical device (36), a linear magneto-optic garnet (38) and photodetection means (40).

* * * * *